United States Patent [19]

Leveen

[11] Patent Number: 5,010,897

[45] Date of Patent: Apr. 30, 1991

[54] APPARATUS FOR DEEP HEATING OF CANCER

[76] Inventor: Harry H. Leveen, 321 Confederate Cir., Charleston, S.C. 29407

[21] Appl. No.: 343,832

[22] Filed: Apr. 26, 1989

[51] Int. Cl.$^5$ .............................................. A61N 1/40
[52] U.S. Cl. .................................. 128/804; 600/13
[58] Field of Search ...................... 128/804; 600/13, 14

[56] References Cited

U.S. PATENT DOCUMENTS

| | | | |
|---|---|---|---|
| 3,457,924 | 7/1969 | Kendall | 128/804 |
| 4,028,518 | 6/1977 | Boudouris et al. | 128/804 X |
| 4,230,129 | 10/1980 | LeVeen | 128/804 |
| 4,269,199 | 5/1981 | Armitage | 128/804 |
| 4,674,481 | 6/1987 | Boddie, Jr. et al. | 128/804 |
| 4,702,262 | 10/1987 | Andersen et al. | 128/804 |

FOREIGN PATENT DOCUMENTS 2027594  2/1980  United Kingdom ................ 128/804

*Primary Examiner*—Lee S. Cohen
*Attorney, Agent, or Firm*—Gipple & Hale

[57] ABSTRACT

An apparatus for the deep heating of cancers employing two single turn coaxial coils of varying diameter ranging from 2 inches to 6 inches which rotate synchronously in planes which are parallel to each other with the central axis of each coil lying in exactly the same line which is perpendicular to the plane of the coil. When the two coils are at 180° from each other a line drawn through the central axes of both coils traverses the center of a tumor in the body which is to be heated and is not perpendicular to the two planes of rotation. The coils are placed so that the inner curvature of the rotating coil is tangential to the center of the tumor mass with the summated magnetic field of the rotating coils continuously heating the tumor with the maximum number of lines of magnetic force.

17 Claims, 3 Drawing Sheets

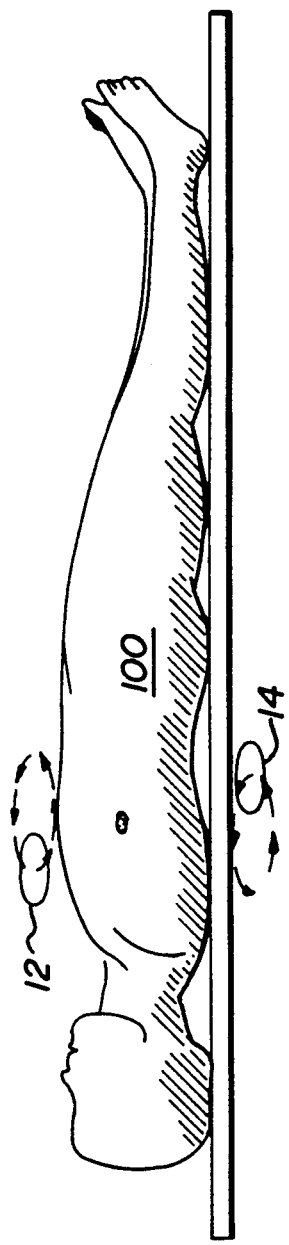
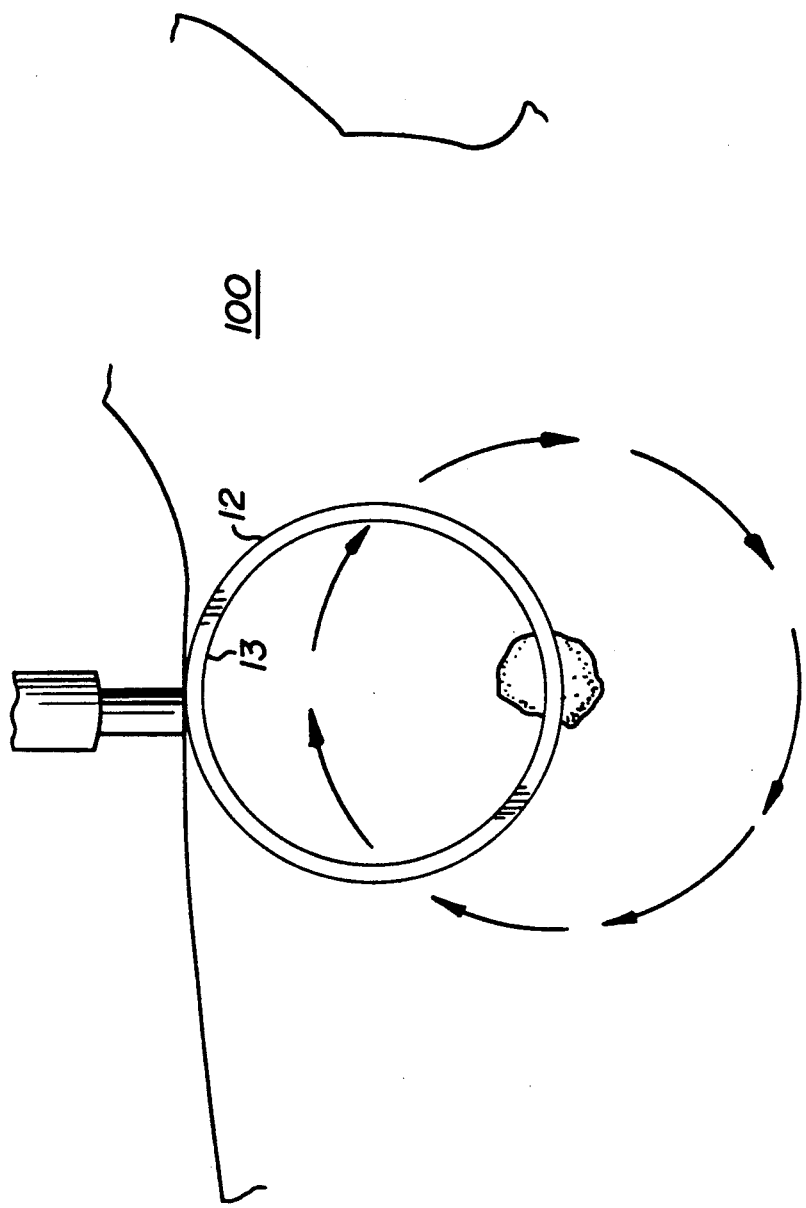
FIG. 1
FIG. 2

APPARATUS FOR DEEP HEATING OF CANCER

BACKGROUND OF THE INVENTION

This invention relates to the treatment of tumors in animal hosts, such as human beings, and in particular provides a technique for destroying the tumor without injury to adjacent normal tissue. The tumors can be either benign or malignant and include carcinomas, sarcomas, cysts and avascular lesions.

It is an important object of this invention to provide an apparatus applicable to the treatment of tumors under a wide variety of conditions which can be utilized with a minimum, and preferably an absence, of surgery.

It has been noted that tumors can be affected by hyperthermia (Brit. of Cancer 25:771, 1971; Cancer Research 32:1916, 1972) and this observation was coupled with the notation that the tumors were heat sensitive. Experiments with external surface heating do not produce deep heating and in some cases, using hyperthermia, the whole animal was heated as much as the tumor. Others have felt that a slight raise in temperatures produced by metabolic changes in the cancer interfered with cell growth (Europ. J. Cancer 9:103, 1973). Still others have heated tumors for a few degrees by diathermy and observed that the effect on the tumor was inhibitory but not obstructive (Zeit. fur Naturforschung 8, 26:359, 1971). There is still disagreement in the role heat may play in the treatment of cancer (The Lancet, May 3, 1975; 1027).

Anatomical studies suggest that the blood flow through carcinomas and other neoplasms is sluggish (Acta Pathalogica Microbiologica Scand., 22:625, 1945; Advances in Biology of the Skin, 21:123, 1961). Furthermore, tumors possess an angiogenetic factor which initiates the formation of new blood vessels. These blood vessels, however, are capillaries which because of their small diameter offer great resistance to blood flow. The capillaries make connections with the normal capillaries on the periphery of the tumor and form tortuous haphazard pathways before emptying into some small vein at the periphery of the tumor. Frequently, there is marked venous obstruction within the tumor caused by compression of the peripheral veins due to enlargement of the tumor and sometimes due to ingrowth of tumor cells into the blood vessels obstructing them.

Anatomical studies also demonstrate the presence of arterio-venous fistulae at the periphery of tumors which can cause the tumors to appear vascular and angiographic because of the rapid appearance of contrast media, but which actually deprive the tumor of the blood supply. The arterio-venous fistulae at the periphery of the tumor tend to create a low resistance pathway at the surface of the tumor which lowers the arterial pressure and diverts blood from entering the tumor.

Although anatomical studies suggest that the tumor blood flow is diminished and slow, angiographic studies have functionally confirmed that blood flow through tumor is actually sluggish. Residual contrast medium remains in the tumor after it has been swept out of the adjacent normal tissue by normal blood flow. This remaining residual contrast medium has been called a "Tumor Stain". The tumors which have been studied radiographically have been brain tumors and kidney tumors.

This has been confirmed by the applicant by the indicator dilution technique measuring the actual flow of blood through normal tissue and through tumors. The indicator dilution technique is more reliable than the visual method as seen on angiography. Such studies were done in vivo using X-ray contrast medium dilution and in vivo on excised specimens. In the excised specimens blood flow was measured by indicator dilution technique using radioiodinated serum albumin. The albumin molecule was tagged with $I_{131}$ and the isotope dilution was measured in the tumor and in normal tissue by a columnated scintillation counter. These studies indicated that the magnitude of flow through the adjacent normal tissue is such that the tumor tissue is differentially heated when the area of body containing the tumor is treated by diathermy.

It is known that tumors are usually destroyed by a quantum of heat which would be delivered by a temperature of 45° C. over a period of three hours. Exposure at higher temperatures requires less time. At 50° C., the time is reduced to a mere ten minutes. Such temperatures, of course, also destroy or severely damage normal tissue and the present invention utilizes Applicant's prior discovery that when a portion of the body is heated, for example, by applied radio frequency electromagnetic radiation, the tumor is heated differentially to a greater extent, such that the temperature of the normal tissue adjacent the tumor can be kept below 40° C.

This effect is caused primarily by the normal blood flow in the adjacent normal, non-cancerous tissue, because the temperature at which tissue is heated is a function of the blood supply to the tissue. Although the blood itself is heated, it serves to carry heat away from the part being heated. Tissues which are poorly perfused with blood such as cancerous tissue become heated more rapidly and to a higher temperature than tissues which have a normal rate of blood flow. As pointed out above, cancerous and other malignant and benign growths develop outside a preformed blood distribution network and derive their blood supply from the periphery of the tumor where it meets the adjacent normal blood supply. As a consequence, the slow rate and volume of blood flow through the tumor provides a lessor cooling rate in &he tumor than the flow of blood through the normal tissues adjacent the tumor.

Such treatment of cancer has been fully disclosed in Applicant's U.S. Pat. No. Re. 32,066 dated Jan. 21, 1986 and the references cited therein.

The apparatus for heating tumors in the '066 patent employed an amplifier which amplified the output of a crystal oscillating at 13.56 or 27.12 megaHertz. Crystal oscillators are used to insure that the generated frequencies were within the band width allocated to medical use, otherwise it would be necessary to place the patient together with the R.F. generator into a Faraday cage to shield against leakage into the environment. However, studies on patients during R.F. treatment disclosed that the amount of R.F. in the immediate environment was usually greater than that permitted OSHA standards.

U.S. Pat. No. 4,285,346 describes an impedance matching unit which may be used between a radio frequency generator or source and a pair of electrodes placed adjacent a body. The patent also describes arrangements using a plurality of pairs of electrodes, pairs of which may be rendered separately inoperative by grounding of the transmission cable extending from the matching unit to a pair of electrodes.

U.S. Pat. No. 4,269,199 describes a method for inducing local hyperthermia in a tumor using an induction coil which is moved over a portion of the body containing the tumor such that the axis of the coil constantly transects different portions of the tumor.

Canadian Patent No. 1,177,895 describes dual and single coils which are excited in flux-aiding relationship over a small space in relation to the inside coil diameter. The inside diameter of the coils should be at least 1.5 times the diameter of the effective cell treatment zone and the coil spacing is substantially equal to the inside coil diameter which lends itself to testing on small animals and shallow seated cancer tumors.

U.S. Pat. No. 4,356,458 describes an apparatus for automatically adjusting the impedance of an electrical circuit connected to a radio frequency source so as to maintain the impedance of the circuit at a substantially constant value to permit the maximum transfer of energy to the load forming part of the circuit, and relates particularly to apparatus for use with the short wave diathermy apparatus described in the above-mentioned '346 patent.

U.S. Pat. No. 4,230,129 relates to apparatus for connecting radio frequency treatment equipment to the output of a body scanner or the like such that the exact position and configuration of the tumor can be plotted in terms of rectangular coordinates and the radio frequency equipment can then be directed or focused precisely on the tumor location in order to avoid excessive heating or thermal damage to the surrounding tissue. The applicator plates or discs are moved in an orbital manner such that the tumor always lies on the axis between the applicator plates and the radio frequency energy is concentrated therein. Because of the orbital movement of the applicators, the energy is not continuously being applied to a confined area, i.e., to immediately surrounding tissue but is rather applied over a comparatively large surface area so as not to affect the surrounding tissue adversely.

BRIEF DESCRIPTION OF THE DRAWINGS

FIG. 1 is a side elevational view of a patient with the invention shown in schematic;

FIG. 2 is a plan view of the invention with the frequency emitting coil of the invention placed over the chest area of the patient;

DETAILED DESCRIPTION OF THE INVENTION

Figure 3:
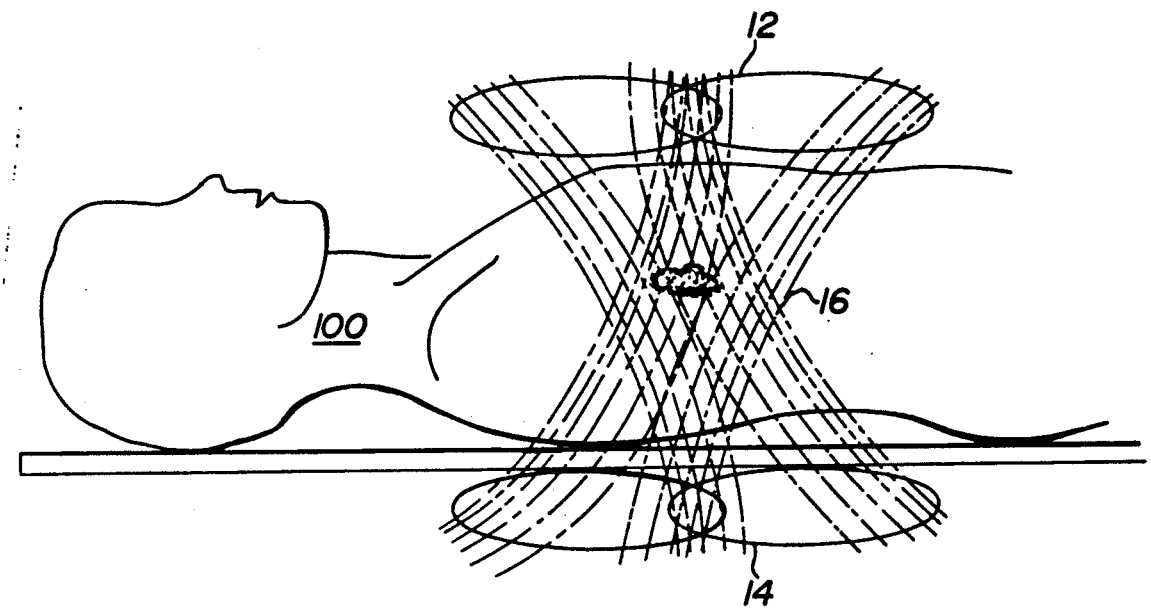
FIG. 3 is a schematic view of the actuated coils and electromagnetic waves.

The best mode and preferred embodiment of the invention is shown in FIGS. 1-5.

A practical method for heating deep lying malignant tumors has not been achieved although some attempts have been made to solve this problem by a pulsed phase array as is shown by U.S. Pat. Nos. 4,341,227, 4,448,198 and 4,633,875. Such apparatus, is costly and unfortunately uses wavelengths in the range of 900 megaHertz which are rapidly absorbed by human tissue. The absorption coefficient of longer wavelengths from 100 kiloHertz to 25 megaHertz is much lower; and therefore, these frequencies penetrate deeply into the body. Waves having lengths over a meter cannot be focused and require shielded rooms and thus are not favored by manufacturers than who prefer wavelengths of 1 cm. or less. OSHA standards were set to protect technicians and personnel in the immediate environment of an R.F. generator who might receive doses larger than those permitted by OSHA standards. Such a situation is considered unhealthy by OSHA and therefore prohibited. Therefore, in such conditions it is mandatory to enclose the patients in isolated enclosures during therapy. This was found to be true for both 13.56 and 27.12 megaHertz uses regardless of whether the heating was by induction or dielectric means. The patient, especially if obese, became an antennae with radiant power of sufficient magnitude to contaminate the immediate environment in excess of the criteria specified by the OSHA standards.

Since the patient must be placed in a Faraday enclosure, regardless of the type of equipment used, there does not appear to be any need to use a crystal oscillator and an expensive amplifier An inexpensive self-exciting unit will obtain the same results. With a self-exciting tank unit to generate the R.F., the wavelength changes slightly to match the inductance and reluctance of the load and expensive automatic matching circuits become unnecessary. The response times of present impedance matching networks proved to be inadequate for rotating electrodes.

As previously stated very short wavelengths in the range of 400 to 1000 megaHertz can be better focused as compared to longer wavelengths of 10 to 30 megaHertz. These later wavelengths are too long to be focused. However, this defect can be overcome by shaping the magnetic field, which produces a type of focusing.

In previous U.S. Pat. Nos. 3,362,740, 3,984,223 and 4,230,129 different methods to shape an electromagnetic field are described. Therefore, it is possible to spatially alter the summated field strength by rotating a coil which emits a magnetic field as U.S. Pat. No. 4,269,199 describes. The field can also be shaped by placing a tuned circuit oscillating at the same frequency into the area of a coil emitting a magnetic field as is shown by U.S. Pat. No. 4,011,234.

Furthermore, two coils placed on the anterior and posterior surface of the body produce magnetic fields whose lines of force pass through the body as is set forth in U.S. Pat. No. 4,011,234 and as confirmed in the literature. (Radiation Research 95: 175 1983) This occurs whether both coils are activated or when only one coil is activated.

As shown in FIG. 1 the present invention uses at least one pair or pairs rotating coils 10 and 14 which are widely spaced apart a distance greater than the diameter of the smallest coil to repeatedly distribute the heating energy over a wide portion of the body 100 as they rotate to treat the deep seated tumor. Each coil is a single turn coaxial coil ranging in diameter from 2 to 6 inches. The coils rotate synchronously in planes which are parallel to each other. Any mechanical drive known in the art with a motion translator assembly can carry the coils in the rotative manner described. However, the coil holder must be constructed of an insulated material. The Colpitts circuit as later described is mounted on the coil housing and power is carried by a flexible conduit to the circuit. The central axis of each coil lies in exactly the same line which is perpendicular to the plane of the coil. When the coils are at 180° from each other, a line drawn through the central axis of both coils traverses the center of a tumor in the body which is to be heated. The radius of rotation is the same as the diameter of the coil with the inner edge 13 of the single turn coil 12 being tangential to the center of the tumor 101 so that the tumor is thus placed under constant heating. Another coil 14 rotates on the opposite side of the body 100 adjacent a non-conductive table 98 at 180° past the primary coil or in a direction appropriate with the primary coil. The magnetic lines of field 16 between the two coils is shown in FIG. 3 to heat the tumor.

When induction heating is employed, the skin is unavoidably heated. This is without consequence since the skin can be cooled by blowing refrigerated air over it, or cooling with a pad 40. The pad 40 is made of two vinyl sheets which are sealed together to form a fluid channel 42. Suitable non-conductive refrigerant fluids can be used for example, distilled water or diethylene glycol.

Figure 5:
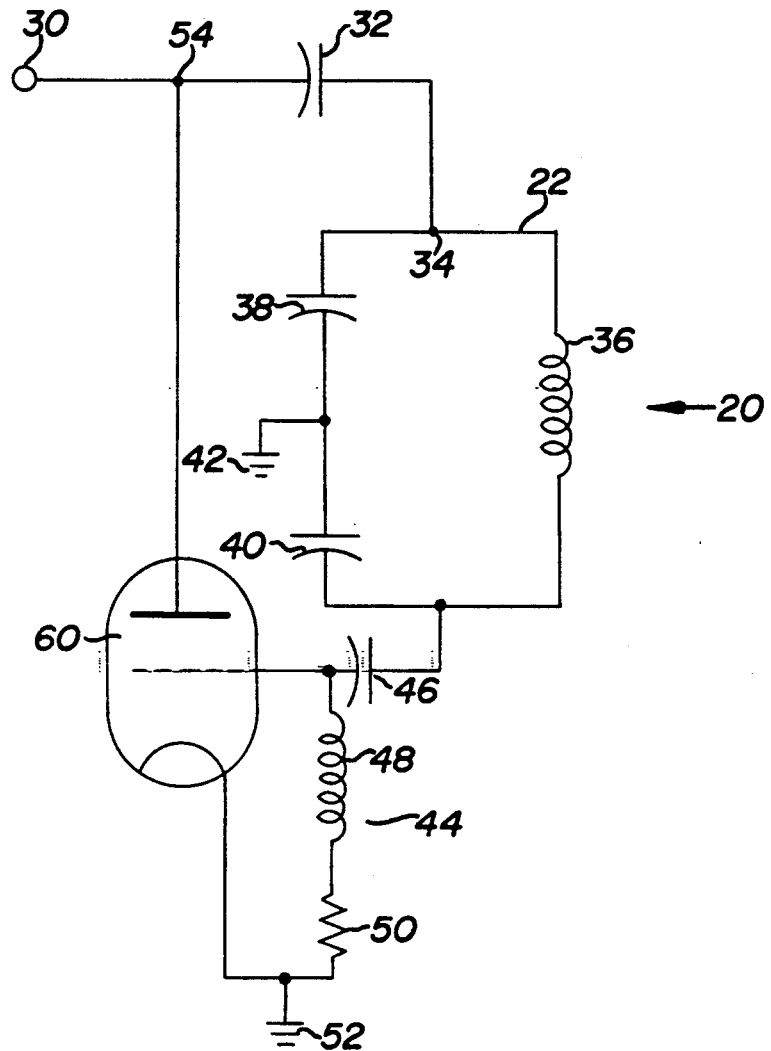
FIG. 5 is a schematic of a Colpitts type of excitation circuit used in the invention.
Figure 6:
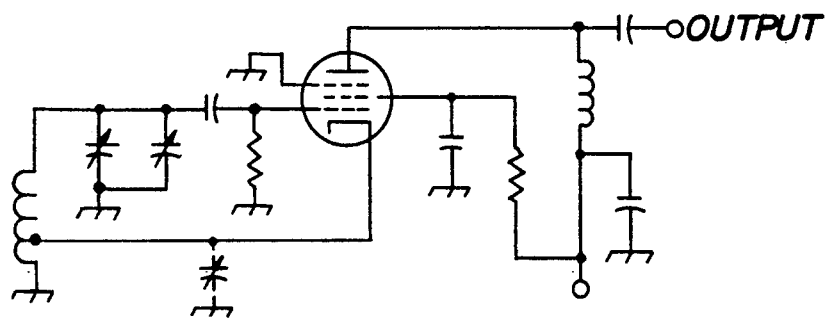
FIG. 6 is a schematic of one alternate schematic prior art Hartley type excitation circuit.

The apparatus utilizes a Colpitts type circuit 20 which is a self tuning radio frequency (R.F.) generator using a LC tank circuit 22 and an industrial triode valve 20 as shown in FIG. 5. The Colpitts tank type R.F. generator comprises a power supply 30 which feeds power across capacitor 32 into node 34 of the tank circuit 22. The tank circuit is provided with an inductor coil 36 which changes the voltage to the desired R.F. wavelength depending on the length of coil and balancing capacitors 38 and 40 which are in series. A ground 42 is positioned therebetween for grounding purposes. Since a feed back of the tank circuit 22 is not desired, the tank circuit develops a small R.F. and the Thyraton tube 60 amplifies it. The tank circuit 22 feeds an inverter circuit 44 comprising capacitor 46, coil 48, resistor 50 and ground 52. The inverter circuit operates the grid of the thyraton tube 60. The thyraton tube 60 generates the desired R.F. pulse into input 54. The type of circuit which has been found most suitable is generally called a Colpitts type circuit which is well known in the art. Other circuits which could be utilized are the coupled-grid reverse feedback (tickler circuit) or a Hartley circuit as shown in FIG. 6 and labeled prior art. The Colpitts circuit differs from the other circuits in that the grid drive is obtained by using a capacitance voltage divider. The only disadvantage which the Colpitts circuit has over the Hartley circuit is that the Colpitts circuit uses two tank capacitors 38 and 40 instead of one which increases the cost. Nevertheless, it is more satisfactory for frequencies above 5 Mhz. and has the advantage that the phase reversal is exactly at 180°. Parasitic oscillations arising from stray lead inductances resonating with the valve and intra-electrode capacitances are less likely to occur with the Colpitts circuit.

The use of a LC tank circuit appreciably reduces the cost of the R.F. power over the amplification of a fixed crystal frequency. The high cost of the amplifiers and automatic impedance matching makes the fixed frequency amplification method very costly. Frequencies with the circuit described can be made to conform to the ranges allocated by the FCC but a radiation screen is nevertheless necessary to protect the operator.

This application incorporates by reference U.S. Pat. No. Re 32,066 issued Jan. 21, 1986 as showing examples of treatment showing the R.F. wavelengths of the present invention.

Figure 4:
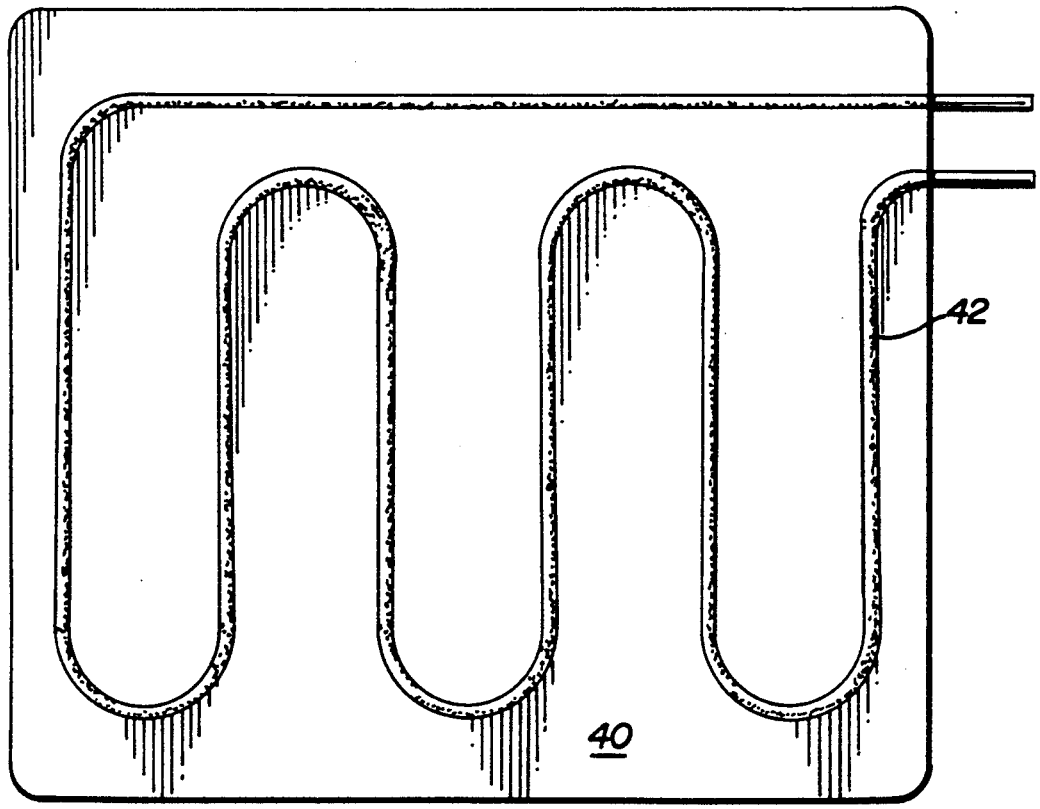
FIG. 4 is a plan view of a refrigerated pad used in the invention.

Thermotherapy lung cancer is exceedingly difficult because the tumor may be surrounded by an air containing lung which offers high impedance to dielectric type of heating where the electrodes are capacitor plates. Inductive heating with 27.12 MHz. heats the tumor extremely well. The skin containing blood is heated but can be cooled by refrigerated pads 40 which are transparent to the magnetic field through which refrigerated non-electrolytic fluids are pumped as shown in FIG. 4. Fat also contains little blood or other conductive material and does not absorb the R.F. energy. Although muscle does absorb some of the energy the rotating electrodes cause this tissue to be heated only intermittently and over a wide area. An inflated lung has poor conductivity and is only slightly heated. The tumor however contains electrolytes and is intensely heated. Since the tumor is cooled by blood flow and since blood flow through tumors is sluggish the lung cancer can be heated to temperatures of 44°-45° C. without damage to adjacent tissue. Because the tumor is perfused principally by blood from the bronchial artery, the bronchial artery can be occluded angiographically if there is difficulty reaching the desired temperature.

While the general embodiments of the present invention have been described, it will be apparent to those of ordinary skill in the art that various alternative configurations and embodiments can readily be adapted to the present invention and are considered to fall within the scope thereof as set forth in the following claims.

What is claimed is:

1. An apparatus for developing radio frequency energy between spaced coils to apply an electromagnetic field between the coils to heat a tumor deep seated in a human body comprising a pair of spaced coils spaced apart a distance greater than the diameter of the smallest coil, a radio frequency generator means which generates radio frequency waves to at least one of said coils, means to rotate said coils so that one coil is movably positioned from one surface of the body and the other coil is movably positioned from another surface of the body with both coils being movably positioned from the respective surface of the body to move synchronously in planes which are parallel to each other to maximize magnetic lines of force on said tumor.

2. An apparatus as claimed in claim 1 wherein said generator means comprises a thyraton tube, a tank circuit which converts a current to a radio frequency wave length and an inverter circuit electrically connected to said tank circuit which operates a grid of said thyraton tube.

3. An apparatus as claimed in claim 1 wherein said generator means is a Colpitts type radio frequency tank circuit.

4. An apparatus as claimed in claim 2 wherein said tank circuit includes an inductor coil which determines said radio frequency wave length in a range of 10 to 30 megaHertz.

5. An apparatus as claimed in claim 1 wherein said means to rotate said coils is adapted to rotate said coils so that an inner portion of at least one coil is positioned tangent to a tumor in a human body placed between said coils.

6. An apparatus as claimed in claim 1 wherein said generator means puts out a frequency of 10 to 100 megaHertz.

7. An apparatus as claimed in claim 1 wherein said generator means is a Hartley radio frequency circuit.

8. An apparatus as claimed in claim 1 wherein said generator means is a coupled grid reverse feedback tank radio frequency circuit.

9. An apparatus as claimed in claim 1 wherein said coils comprise two single turn coaxial coils.

10. An apparatus as claimed in claim 9 wherein the diameter of each coil ranges from 2 to 6 inches.

11. An apparatus as claimed in claim 9 wherein the central axis of each coil lies on the same line which is perpendicular to the plane of the coil.

12. An apparatus for the treatment of deep seated tumors in human bodies comprising spaced apart coils adapted to receive a human body therebetween for producing a field of electromagnetic energy in a radio frequency range ranging from 10 to 30 megaHertz, said coils being disposed in a circuit comprising a self tuning radio frequency generator which generates and transmits radio frequency energy to said coils and drive means with a motion translator assembly to rotate said coils synchronously in planes which are parallel to each other so that lines of magnetic force are generated between them to cause continuous heating of said tumor.

13. The apparatus of claim 12 wherein said spaced apart coils are 180° from each other and coaxial.

14. An apparatus for the treatment of tumors in human bodies which comprises a pair of spaced apart coils for producing a shaped field of electromagnetic energy therebetween in a radio frequency range which ranges from 10 to 30 megaHertz, means to rotate said pair of coils synchronously in parallel planes to each other, each coil of said pair of coils having a diameter ranging from 2 to 6 inches and being placed so that the inner curvature of each rotating coil is tangential to the center of a tumor mass, said coils being spaced apart a distance greater than the diameter of one of said coils to repeatedly distribute the heating energy over a wide portion of a human body placed therebetween, said coils being disposed in a circuit comprising a self tuning radio frequency generator which generates and transmits radio frequency energy to said coils so that lines of magnetic force are generated between them during rotation to cause continuous heating of said tumor.

15. An apparatus as claimed in claim 14 wherein said circuit comprises a power supply electrically connected to a tank circuit, said tank circuit being provided with an inductor coil having balancing capacitor means which changes voltage to a desired R.F. wavelength and amplifier means to generate an R.F. pulse.

16. An apparatus as claimed in claim 15 wherein said balancing capacitor means comprises a plurality of capacitors connected in series.

17. An apparatus as claimed in claim 15 wherein said amplifier means comprises an inverted circuit which operates the grid of a thyrator tube which generates said pulse.

* * * * *